United States Patent [19]
Cueman et al.

[11] Patent Number: 5,235,856
[45] Date of Patent: Aug. 17, 1993

[54] DYNAMIC ULTRASONIC GAUGE APPARATUS WITH A FERRULE MOUNTING TO POSITION A TRANSDUCER

[75] Inventors: Michael K. Cueman, Niskayuna; George C. Sogoian, Glenville; John J. Kaehler, Scotia, all of N.Y.; Paul B. Tuck, Wilmington, N.C.; Steven R. Hayashi, Schenectady, N.Y.

[73] Assignee: General Electric Company, Schenectady, N.Y.

[21] Appl. No.: 908,207

[22] Filed: Jul. 2, 1992

[51] Int. Cl.$^5$ ............................................. G01N 29/026
[52] U.S. Cl. ............................................. 73/622; 73/644
[58] Field of Search ........................... 73/622, 629, 644

[56] References Cited

U.S. PATENT DOCUMENTS

| | | | |
|---|---|---|---|
| 3,190,112 | 6/1965 | Beaujard et al. | 73/644 |
| 3,472,065 | 10/1969 | Maxwell | 73/597 |
| 3,672,211 | 6/1972 | Hatch | 73/633 |

FOREIGN PATENT DOCUMENTS

| | | | |
|---|---|---|---|
| 504151 | 2/1976 | U.S.S.R. | 73/644 |
| 2064773 | 6/1981 | United Kingdom | 73/644 |

OTHER PUBLICATIONS

Bronnikov et al., "Instrument for the Automated Resonance Inspection of Pipe Wall Thickness," 1974, pp. 298–300.

Primary Examiner—Hezron E. Williams
Assistant Examiner—Nashmiya Ashraf
Attorney, Agent, or Firm—James E. McGinness; James Magee, Jr.

[57] ABSTRACT

An ultrasonic gauging apparatus is disclosed suitable for dynamic ultrasonic gauging in the harsh environment of a tube forming operation. An ultrasonic transducer is positioned in a tubular member by a ferrule mount. The tubular member is attached to a platform having spring biasing that permits limited motion of the transducer while maintaining a preselect orientation of the transducer relative to the tube.

13 Claims, 3 Drawing Sheets

DYNAMIC ULTRASONIC GAUGE APPARATUS WITH A FERRULE MOUNTING TO POSITION A TRANSDUCER

This application is related to copending application Ser. No. 908,208, filed Jul. 2, 1992.

This invention relates to an ultrasonic gauging apparatus, and in particular to dynamic ultrasonic gauging, i.e., continuous measurement of a moving body.

BACKGROUND OF THE INVENTION

Ultrasonic gauging employs sound waves or mechanical vibrations whose frequency is above the audible range in the frequency spectrum. The sound is produced by a transducer exhibiting piezo electric properties where electrical energy is converted into mechanical vibrations or, conversely, mechanical vibrations are converted into an electrical signal. Thus, the transducer can be used to transmit ultrasonic waves and to detect or receive the waves. The sound produced by the transducer is introduced into the body to be gauged through a liquid couplant such as water or oil, and generally propagates in a fairly well defined beam through the material. The propagation continues until some or all of the sound is reflected by a boundary, for example, the inner wall of a tube.

Specialized techniques have been developed to extend the usefulness of the ultrasonic equipment. One apparatus, known as a bubbler, consists of a semicontained liquid column. The transducer is sealably mounted in one end of the column, and the body being gauged substantially covers the other end. There can be some leakage of couplant where the body covers the column end, and the leakage can be minimized by proper design. The bubbler provides a solid column of water substantially free of air bubbles between the transducer and the body being gauged. A completely free flowing liquid column can be used where the motion or temperature of the body being gauged is excessive.

The pulse-echo technique of ultrasonic gauging employs a short burst of ultrasonic energy known as the initial pulse. It is transmitted into the body by the transducer through the coupling medium. The ultrasonic impulse travels in essentially a straight line until it strikes a reflecting surface such as the oppositely facing tube surface. The ultrasonic reflection of the wave from the surface is governed by well known laws, analogous to the laws of optics. Any of the reflected energy that returns to the transducer is detected as an echo signal, and its amplitude and location in time are related to the thickness of the tubing wall. To measure the wall thickness of a cylindrical body, the pulse-echo ultrasound measurement requires precise alignment and focusing of the ultrasound beam with the body.

For example, ultrasound can be used to measure the wall thickness of a tube by timing the interval between reflections of the sound wave from the inner and outer surfaces of the wall. The transducer must be aimed so that the beam of ultrasonic waves is directed radially to the cylinder axis, herein referred to as the reference axis, and focused at a preselected location within the wall or inner diameter of the tube. Misalignment of the transducer can cause attenuation of the reflected sound waves, and an incorrect measurement of the wall thickness.

However, as a tube is processed through a tube forming apparatus it is subjected to vibrating motion. For example, in a pilger mill the oscillating motion of the rolling dies and exit turning jaws of the mill induce a strong vibrating motion in the tube. As a result, it is difficult to provide the necessary orientation between the tube and the ultrasonic transducer for dynamic ultrasonic gauge measurement of the tube wall thickness during manufacture of the tube.

One aspect of this invention is to provide an ultrasonic gauging apparatus that provides a preselected orientation between a cylinder, and an ultrasonic transducer.

Another aspect of this invention is to provide an ultrasonic gauging apparatus that provides a preselected orientation between an ultrasonic transducer, and a cylinder subject to vibrating motions.

BRIEF DESCRIPTION OF THE INVENTION

An ultrasonic gauging apparatus comprising, a channel means having a top and a bottom, with a cavity extending across the top having sidewalls for maintaining a preselect orientation with a reference axis of a cylinder in contact with the sidewalls. The channel means having a first bore extending from the bottom to the cavity normal to the reference axis, and a water inlet bore extending from the first bore through the channel means. A platform means operatively mounted to the channel means bottom having biasing means for biasing the channel means against the cylinder while allowing the channel means to follow vibrating motion of the cylinder.

A cylindrical mounting means is attached to the channel means bottom, having a second bore axial to the first bore. The cylindrical mounting means extends into the first bore mating therewith, and extends from the channel means bottom to a ferrule mounting means for adjustably mounting a cylinder in the second bore so that it can be positioned normal to the reference axis and provide a waterproof seal therebetween.

An ultrasonic transducer can be mounted in the ferrule means, which permits aiming of the transducer so that the ultrasonic beam is radial to the reference axis and focused to a preselected area of a cylinder in the cavity to provide accurate ultrasonic gauging of the cylinder wall.

DETAILED DESCRIPTION OF THE INVENTION

The apparatus of this invention provides a preselected orientation between an ultrasonic transducer and the axis of a cylinder, despite vibrating motion of the cylinder. As a result, dynamic accurate ultrasonic gauge measurements can be made on a tube as it is processed in a tube reduction operation such as a pilger mill.

Figure 1:
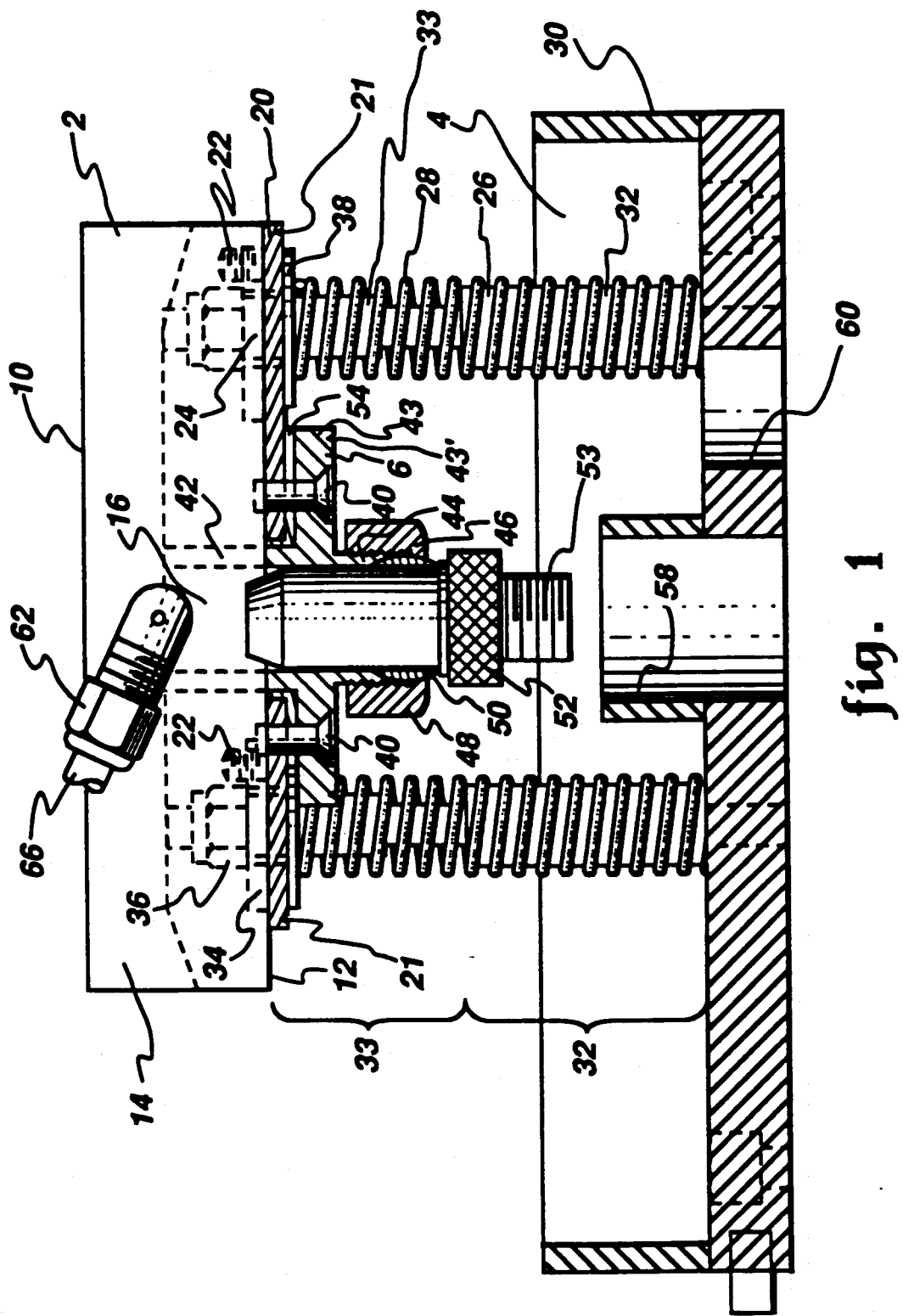
FIG. 1 is a side view of a partial cross section of a dynamic ultrasonic gauging apparatus.

Referring to FIG. 1, the apparatus of this invention is comprised of a channel means 2, a platform means 4, and a cylindrical mounting means 6. The channel means 2 is formed from a non-abrading wear resistant material such as plastic having a high durometer hardness, e.g., polyurethane or nylon. The channel means has a top 10 and a bottom 12 with a channel 14, also shown in FIGS. 2 and 3, extending across the top 10. The cavity sidewalls 15 (shown in FIG. 3) are configured for maintaining a preselect orientation with a reference axis of a cylinder in the cavity. For example, the cavity sidewalls 15 can be v-shaped so that the reference axis of the cylinder in contact with the cavity sidewalls is parallel to the apex of the v-shaped cavity.

The channel means 2 is formed with a first bore 16 extending from the bottom to the cavity normal to the reference axis. A water inlet bore 18 extends from the first bore 16 through the channel means, to provide a passage for introducing a flow of water into the first bore 16.

Figure 2:
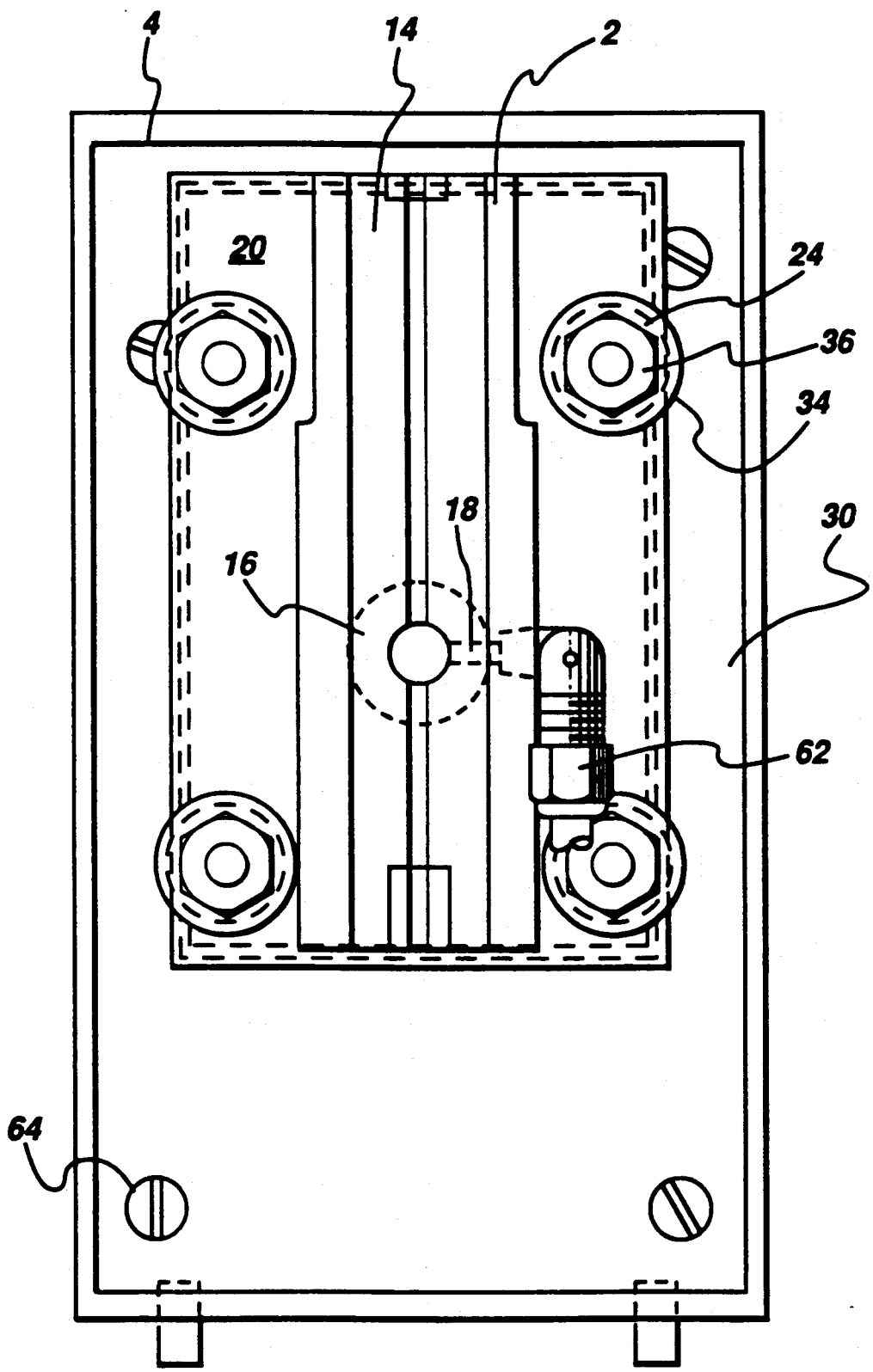
FIG. 2 is a top view of the ultrasonic gauging apparatus shown in FIG. 1.
Figure 3:
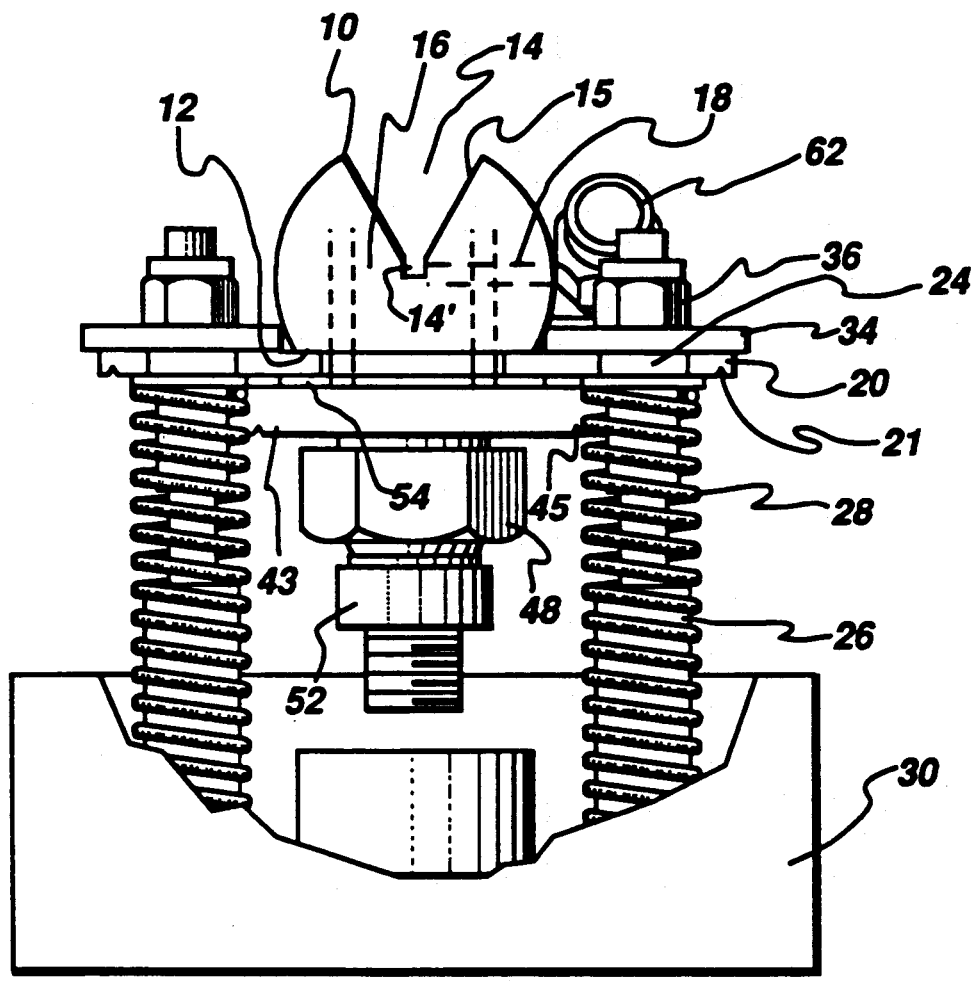
FIG. 3 is an end view of the ultrasonic gauging apparatus shown in FIG. 1.

The platform means 4 is comprised of a plate 20, rods 26, spring means 28, and basin 30, preferably formed from a suitable steel. The plate 20 is attached to the bottom of channel means 2 by conventional fasteners 22, and is formed from a rigid corrosion resistant material such as stainless steel. The plate 20 extends beyond the bottom of channel means 2, as shown in FIG. 2, and is formed with holes 24 having a first diameter suitable for accepting rods 26.

The basin 30 is formed from a corrosion resistant material such as stainless steel, and is configured for capturing water flowing from channel means 2. The rods 26 extend from basin 30 at positions suitable for supporting channel means 2, for example, at corners of a square as shown in FIG. 2. The rods 26 can be mounted in threaded bores in the basin 30 by forming mating threads at the rod ends. The rods 26 have a second diameter less than the first diameter of holes 24, for example about 6 millimeters less, suitable for allowing the plate 20 limited movement in the plane of the plate to follow vibrating motion of the cylinder. The rods 26 extend through holes 24 in the plate 20 to a stop means mounted on the rods, such as washers 34 and lock nuts 36. The washers having a diameter greater than the second diameter of rods 26, and less than the first diameter of the holes 24 to minimize intrusion of the stop means into the holes.

The springs 28 are positioned on rods 26, with second washers 38 between the plate 20 and the springs 28. The springs 28 bias the channel means 2 towards the cylinder in contact with the cavity 14. The washers 38 have an inside diameter that is larger than the second diameter of rods 26, and an outside diameter larger than the holes 24 to prevent the springs from intruding into the holes. In this way, the platform means allows movement in the direction normal to the plate 20 while supporting the channel means 2 in a desired orientation to the cylinder in contact with the cavity sidewalls 15. The platform means provides a limited range of motion in any direction sufficient for the channel means 2 to follow the vibrating motion of the cylinder.

The springs 28 have a spring rate high enough to provide a natural vibration frequency of the apparatus that is higher than the vibrating frequency of the cylindrical body in contact with the channel means 2. Preferably the spring rate is sufficiently low to minimize abrasion of the cylinder. By minimizing the mass of the apparatus supported by the springs 28, the natural vibration frequency of the apparatus is reduced, and the spring rate can be lowered. Preferably, the channel means 2, plate 20, and cylindrical mounting means 6 are configured to minimize their mass, to lower the natural vibration frequency of the apparatus. In this way, the spring rate of springs 28 can be minimized, while providing the spring rate high enough to provide a natural vibration frequency of the apparatus that is higher than the vibrating frequency of the cylindrical body.

Preferably, the rods 26 have a first section 32 extending from the basin 30 to a second section 33 that extends to the stop means. The first section of rods 26 having a third diameter greater than the inside diameter of second washers 38. This limits the travel of the plate 20 towards the basin 30 to minimize or prevent contact between the cylindrical mounting means 6 and the basin.

The cylindrical mounting means 6 is comprised of an upper section 42, mid-flange 43, and a lower section 44. The cylindrical mounting means 6 is formed from a rigid corrosion resistant material such as stainless steel. The upper section 42 extends into and mates with first bore 16. The upper section 42 extends from the channel means bottom to the mid-flange 43 fixably attached by conventional fasteners 40 to plate 20. Preferably, the transducer mounted in the cylindrical mounting means is electrically isolated from the forming apparatus the gauge is to be mounted in. Contact between the transducer ground and the ground of the forming apparatus can be minimized or eliminated with electrical insulation 54 between the plate 20 and the mid-flange 43. A suitable electrical insulation material is nylon. Preferably, fasteners 40 are formed from an electrically insulating material such as nylon.

The lower section 44 extends from the mid-flange 43 to a ferrule mounting means 46. The lower section 44 having a threaded outer surface and an inner receiving surface. The ferrule mounting means 46 is comprised of a compression nut 48, and ferrule 50. The compression nut can be formed from a suitable steel, and the ferrule is preferably formed from a electrically insulating material such as nylon. The compression nut 48 mating with the threaded surface of lower section 44, and biasing ferrule 50 against the receiving surface of lower section 44 to form a seal with an ultrasonic transducer 52.

The basin 30 is formed with an annular access channel 58 positioned to provide for a coaxial cable to operatively connect to transducer 52, while minimizing contact with water in basin 30. The basin 30, preferably being formed with a drain 60 for draining water therefrom.

A conventional water supply means 62, for example, an elbow joint having threaded ends connected by a waterproof fitting to water line 66 is threaded into water inlet bore 18 to supply a continuous flow of water to the first bore 16. A cylinder, for example a tube exiting a pilger mill, passes through cavity 14 in contact with cavity sidewalls 15. The apparatus of this invention maintains contact with the tube so that the liquid couplant provides effective coupling of the ultrasonic wave from the transducer 52 to the cylinder. Preferably, the channel means 2 is configured to provide a sufficient flow of water therefrom to minimize the buildup of rolling lubricant from the tube in the channel means, and more specifically in the first bore 16. For example, the apex of v-shaped cavity 14 is formed with a channel 14' (shown in FIG. 3) that provides a flow of water below the tube passing through the cavity 14, washing lubricant from the surface of the tube out of the channel means 2.

Water flowing from the channel means 2 can flow down the outer surface of the apparatus to the transducer 52, and interfere with the coaxial cable (not shown) electrical connection 53. To minimize such flow of water on the outer surface of the apparatus, preferably, the plate 20 is formed with drip rail means 21, and the mid-flange 43 is formed with drip rail means 43'. For example, the drip rail means 21 and 43' can be formed as grooves in the outer periphery of the surface of the plate 20 and mid-flange 43 facing basin 30. Water flowing from channel means 2 down the outer surface of the apparatus flows into the groove which causes the water to collect, form into droplets, and drip therefrom.

The mounting of transducer 52 in cylindrical mounting means 6 by ferrule mounting means 46 not only provides a waterproof seal between the transducer and channel means, but provides a means for positioning the transducer for precise aiming of the ultrasonic wave from the transducer with respect to the cylinder. The compression nut 48 can be loosened so that the ferrule 50 is snug against transducer 52, and permits movement of the transducer. The transducer is positioned so the focused ultrasonic beam is radial to the reference axis, and translated radially to the cylinder axis so that the beam is focused at a preselect location within the tube or cylinder wall. The compression nut is tightened biasing the ferrule 50 against the transducer 52, fixing the desired alignment of the transducer and providing a waterproof seal. The ferrule mounting means provides a fixed mounting for the transducer that is resistant to vibration forces urging the transducer out of the desired alignment.

A preferred apparatus for positioning the transducer within the cylindrical mounting means is shown in co-pending application, Ser. No. 07/908,208 incorporated herein by reference.

The apparatus of this invention can be mounted on a tube forming apparatus, such as a pilger mill, by conventional fasteners 64 (shown in FIG. 2) through the basin 30. The apparatus is mounted so that the platform means 4 biases the channel means 2 against the tube, while allowing the channel means to follow vibrating motions of the cylinder in any direction. Dynamic ultrasonic gauging of the tube exiting the tube forming apparatus can be performed by the apparatus of this invention despite the strong vibrating motion of the tube from the tube forming operation.

What is claimed is:

1. A ultrasonic gauging apparatus comprising; a channel member having a top and a bottom, with a cavity extending across the top having sidewalls for maintaining a preselect orientation with a reference axis of a cylindrical workpiece in contact with the sidewalls, the channel member having a first bore extending from the bottom to the cavity, normal to the reference axis, and a water inlet bore extending from the first bore through the channel member,
 a platform mounted to the channel member bottom, the platform having spring biasing means for biasing the channel member against the cylindrical workpiece while allowing the channel member to follow vibrating motion of the cylindrical workpiece,
 a tubular member attached to the channel member bottom, the tubular member extending into the first bore mating therewith, and extending from the channel member bottom to a ferrule mounting means for adjustable mounting an ultrasonic transducer therein so that the transducer can be positioned normal to the reference axis by vertical or a vial adjustment and provide a waterproof seal therebetween.

2. An ultrasonic gauging apparatus according to claim 1 wherein the channel member is formed from a wear resistant plastic, and the sidewalls form a v-shape.

3. An ultrasonic gauging apparatus according to claim 1 wherein the tubular member is electrically insulated from the platform.

4. An ultrasonic gauging apparatus according to claim 1 wherein the platform is comprised of a basin having rods extending therefrom to support a plate, the plate being mounted to the channel member bottom and having holes with a first diameter for receiving the rods, the channel member being supported over the basin so that water flowing from the cavity falls into the basin, the rods having a second diameter less than the first diameter of the holes, stop means extending beyond the holes mounted on a portion of the rods above the plate, spring means positioned on the rods for biasing the plate towards the stop means, washers positioned on the rods between the springs and the plate to minimize intrusion of the springs into the holes, drain means in the basin for draining water therefrom, the basin having an access channel for permitting a cable to extend therethrough for attachment to the transducer while minimizing contact with water in the basin.

5. An ultrasonic gauging apparatus according to claim 4 wherein the tubular member has an upper section for mating with the first bore, a mid-flange attached to the plate with electrical insulation therebetween, and a lower section having a threaded outer surface and an inner receiving surface, and the ferule mounting means is comprised of a compression nut mating with the threaded surface, and a ferrule biased by the compression nut against the receiving surface to form a seal with the transducer.

6. An ultrasonic gauging apparatus according to claim 5 wherein the rods have a first section having a third diameter extending from the basin to a second section having the second diameter, the third diamter of the rods being greater than the first diamter of the holes and the first section extending from the basin a distance that minimizes contact between the tubular member and the basin.

7. An ultrasonic gauging apparatus according to claim 5 wherein the plate, and the mid-flange each have an outer periphery formed with a drip rail, the drip rail causing water to drip therefrom.

8. An ultrasonic gauging apparatus comprising; a channel member having a top and a bottom, with a cavity extending across the top having sidewalls for maintaining a preselect orientation with a reference axis of a cylindrical workpiece in contact with the sidewalls, the channel member having a first bore extending from the bottom to the cavity, normal to the reference axis, and a water inlet bore extending from the first bore through the channel member,
 a platform comprising a basin having rods extending therefrom to support a plate, the plate being mounted to the channel member bottom and having holes with a first diameter for receiving the rods, the channel member being supported over the basin so that water flowing from the cavity falls into the basin, the rods having a second diameter less than the first diameter of the holes, stop means extending beyond the holes mounted on a portion of the rods above the plate, springs positioned on the rods for biasing the plate towards the stop means, washers positioned on the rods between the springs and the plate to minimize intrusion of the springs into the holes, drain means in the basin for draining water therefrom, the basin having an access channel for permitting a cable to extend therethrough for attachment to the transducer while minimizing contact with water in the basin, a tubular member attached to the channel member bottom, the tubular member extending into the first bore mating therewith, and extending from the channel member bottom to a ferrule mounting means for adjustably mounting an ultrasonic transducer therein so that the transducer can be positioned normal to the reference axis and provide a waterproof seal therebetween.

9. An ultrasonic gauging apparatus according to claim 8 wherein the tubular member has an upper section for mating with the first bore, a mid-flange attached to the plate with electrical insulation therebetween, and a lower section having a threaded outer surface and an inner receiving surface, and the ferrule mounting means is comprised of a compression nut mating with the threaded surface, and a ferrule biased by the compression nut against the receiving surface to form a seal with the transducer.

10. An ultrasonic gauging apparatus according to claim 8 wherein the rods have a first section having a third diameter extending from the basin to a second section having the second diameter, the third diameter of the rods being greater than the first of the holes diameter, and the first section extending from the basin a distance that minimizes contact between the tubular member and the basin.

11. An ultrasonic gauging apparatus according to claim 9 wherein the plate, and the mid-flange each have an outer periphery formed with a drip rail, the drip rail causing water to drip therefrom.

12. An ultrasonic gauging apparatus according to claim 10 wherein the channel member is formed from a wear resistant plastic, and the sidewalls form a v-shape.

13. An ultrasonic gauging apparatus according to claim 11 wherein the tubular member is electrically insulated from the platform.

* * * * *